United States Patent [19]

Bagust et al.

[11] Patent Number: 5,436,005
[45] Date of Patent: Jul. 25, 1995

[54] LOW VIRULENCE INFECTIOUNS LARYNGOTRACHEITIS (ILT) VIRUS FOR VACCINATING BIRDS

[75] Inventors: Trevor J. Bagust, Surry Hills; David R. McGavin, Putney, both of Australia

[73] Assignee: Arthur Webster Pty. Ltd., New South Wales, Australia

[21] Appl. No.: 820,856

[22] PCT Filed: Aug. 1, 1990

[86] PCT No.: PCT/AU90/00322

§ 371 Date: Mar. 5, 1992

§ 102(e) Date: Mar. 5, 1992

[87] PCT Pub. No.: WO91/02053

PCT Pub. Date: Feb. 21, 1991

[30] Foreign Application Priority Data

Aug. 1, 1989 [AU] Australia .............................. PJ5555

[51] Int. Cl.⁶ ....................... A61K 39/245; C12N 7/08
[52] U.S. Cl. ................... 424/229.1; 435/237; 424/816
[58] Field of Search ............ 424/89, 229.1, 816; 435/237

[56] References Cited

U.S. PATENT DOCUMENTS

| | | | |
|---|---|---|---|
| 3,331,736 | 7/1967 | Gelenczei | 424/229.1 |
| 3,444,293 | 5/1969 | Hudson | 424/229.1 |
| 3,950,512 | 4/1976 | Emery et al. | 424/201.1 |
| 4,324,861 | 4/1982 | Kan | 435/237 |
| 4,980,162 | 12/1990 | Honda et al. | 424/202.1 |

OTHER PUBLICATIONS

Izuchi et al, Avian Diseases 27(4):918–926, 1983.
Izuchi et al, Avian Diseases 28(2):323–330, 1984.
Russell et al, Canadian Journal of Comparative Medicine 47(2):163–171, 1983.

*Primary Examiner*—Christine M. Nucker
*Assistant Examiner*—Julie Krsek-Staples
*Attorney, Agent, or Firm*—Fish & Richardson

[57] ABSTRACT

An attenuated infectious laryngotracheitis virus (ILT) that has the antigenic and virulence characteristics of ECACC at Accession No. V89042602, produces an average pock diameter on chorio-allantoic membrane of commercial eggs between 1.0 and 3. mm, exhibits substantially reduced virulence in comparison to ILT SA2 strain, and results in substantially less weight loss in poultry as compared to poultry infected with SA2. A method of producing this ILT virus by serially passaging ILT viral strain SA2 in primary cell cultures followed by serial passaging in embryonated eggs. A method for preventing infection by ILT virus in birds by administering a vaccine with an effective amount sufficient to elicit an immune response.

6 Claims, 1 Drawing Sheet

DNA profiles of 3 strains of ILT virus after cleavage
with restriction endonucleases A, B, C & D;
    N = SA2
    5 = SA2 clone A - cam passage 5
    20 = SA2 clone A - cam passage 20
    S = Salisbury strain (virulent)
restriction endonuclease:
    A = Bam HI
    B = Bgl II
    C = Eco RI
    D = Nae I
DNA molecular weight standards are shown on the left
hand side from 1.3 Kb to 14 Kb

LOW VIRULENCE INFECTIOUS LARYNGOTRACHEITIS (ILT) VIRUS FOR VACCINATING BIRDS

FIELD OF THE INVENTION

The present invention relates to a new strain of infectious laryngotracheitis (ILT) virus for use in vaccinating birds.

ILT virus is a virus of the Herpes family which periodically decimates poultry flocks and its control is therefore of commercial significance. Control is normally by the use of live vaccines and hygiene/quarantine practices. Consequently, the disease is no longer a major disease problem in most countries with a developed poultry industry. However, the threat of explosive ILT in unvaccinated broiler and layer flocks continues due to the persistence of virulent ILT virus in carrier birds present in backyard, fancier and mixed-age flocks.

BACKGROUND OF THE INVENTION

Research has been largely directed toward the empirical induction of protection by live vaccines, together with studies on the protective capacity of humoral antibody against a virulent challenge. Inactivated ILT vaccines have also been used. However, due to the development of resistance and the difficulty in controlling the effect of virulent strains, new forms of vaccination and particularly new virulent strains of the virus are constantly being sought.

The interaction between ILT virus and the host immune system does not generally include infection of leukocytes or viraemia. Cell-mediated immunity is clearly the major mediator of ILT vaccinal protection, with additive effects likely for virus-neutralizing activity detectable in tracheal washings. Protection-inducing components of the ILT virus particle are presently being identified. Antibody studies indicate a substantial antigenic similarity between the major envelope glycoproteins of the wild-type and vaccine strains of ILT viruses.

Historically, the USA and Australia have shared an interest in the control of ILT virus infection since this arian respiratory disease syndrome was recognised in both countries in the mid-1920's. [Hanson, L. E. (1984) in: *Diseases of Poultry*, 8th ed. (M. S. Hofstad and others, eds.), pp 444–451. Iowa State University Press, Ames, Iowa]. The report by Hudson and Beaudette in 1933 of successful ILT vaccination via the vent [Hudson, C. B. and Beaudette, F. R. (1933) *Cornell Veterinarian*, 23: 63–65] was among the first examples of vaccinal control of an avian pathogen. However, some 40 years later in his review of ILT virus and the immune response, Hitchner [Hitchnet, S. B. (1975) *American Journal of Veterinary Research*, 36: 518–519] observed that nearly all subsequent ILT research had been directed towards the empirical aspects of developing partly-attenuated vaccines with assessment of their pathogenicity and the onset and duration of vaccinal protection.

Although it has been substantially controlled by the use of attenuated vaccines in the world's intensive poultry industries [Biggs, P. M. (1982) *Arian Pathology*, 11: 281–300], [Hanson, L. E. (1984) In: *Diseases of Poultry*, 8th ed. (M. S. Hofstad and others, eds.), pp. 444–451. Iowa State University Press, Ames, Iowa], ILT infection and sporadic outbreaks of disease continue to cause difficulties, particularly in multi-age commercial sites.

The main disadvantage of known vaccines to the ILT virus is the high mortality rate caused by using pathogenic isolates. Previous ILT vaccines of low virulence have shown reduced ability to protect birds. The strain SA2 is one of the most commonly used vital strains in Australia at present. This strain has some side effects and can kill 2 to 3% of vaccinated broilers depending on the age of birds and method of husbandry and administration. Although the disease itself can kill 20% of a flock, the sporadic nature of the disease mitigates against the continued use of the SA2 vaccine with its residual virulence, thus enabling the disease to maintain its hold in the poultry population.

DISCLOSURE OF THE INVENTION

The present invention seeks to provide the public with an alternative form of ILT vaccine, and in preferred embodiments, to overcome or substantially ameliorate the problems of the prior art by providing a far less pathogenic virus strain having high immunogenicity. The invention further seeks to provide a commercial ILT vaccine capable of convenient administration such as via drinking water, spray, eye drop or cloacal administration.

In a first aspect the present invention comprises an attenuated ILT virus characterised in that it produces an average pock diameter on chorio-allantoic membrane of commercial eggs of between 1.0 and 3 mm and that the virus exhibits substantially reduced virulence in comparison to ILT SA2 strain and causes substantially less weight loss in poultry in comparison to poultry infected with SA2. Nevertheless the present invention remains highly immunogenic.

In a preferred version of the first aspect the present invention comprises an attenuated ILT virus designated A20, a sample of which was deposited on the 26 Apr. 1989 with the European Collection of Animal Cell Cultures (ECACC), Porton Down, Salisbury, U. K. and allocated the Accession No. V89042602. This strain corresponds to SA2 Clone A passage 20 referred to hereinafter as A20.

This particular strain, and its functional equivalents, is obtained by serially passaging in cell culture the SA2 strain to attenuate the virus. Serial passage of the SA2 virus in primary cell culture caused marked attenuation of pathogenicity between passages 5 and 30. Immunogenicity proved to be inadequate at higher passage levels. The most improved viruses were achieved between passages 5 and 25. After serial passaging on primary cell culture the isolates were further passaged on embryonated eggs via the dropped membrane route for approximately 5 passages.

The deposited ILT strain, A20, and its functional equivalents, have an average pock diameter of between 1.0 and 3 mm on chorio-allantoic membrane of commercial eggs, exhibit substantially reduced virulence characteristics in comparison to SA2, and causes substantially less weight loss in inoculated poultry in comparison to poultry similarly inoculated with SA2, yet remain highly immunogenic.

In a second aspect the present invention consists in a vaccine containing an effective amount of an attenuated ILT strain characterised in that it produces an average pock diameter on chorio-allantoic membrane of commercial eggs of between 1.0 and 3 mm and that the virus exhibits substantially reduced virulence in comparison to ILT SA2 strain and causes substantially less weight loss in poultry in comparison to poultry infected with SA2. In a particularly preferred embodiment of the invention the attenuated ILT strain is the ILT strain deposited with the ECACC under the Accession No. V89042602 and corresponding to SA2 Clone A passage 20 or its functional equivalents.

An effective amount is an amount sufficient to ellicit an immune response. Vaccines made in accordance with the present invention may be administered via oral (e.g. drinking water), aerosol, eye drop or cloacal administration techniques, but not limited to these methods.

The vaccine may also contain other pharmaceutically acceptable compounds or any other antigen or part thereof or may be combined with other viruses or organisms that are used for vaccination.

The vaccines produced in accordance with the present invention exhibit low virulence, provide a duration of protection of at least six weeks and exhibit increased safety in chickens in respect of decreases in flock mortalities and decreases in weight loss in comparison with SA2 vaccines.

In a third aspect the present invention consists of a method for producing attenuated virus for use in a vaccine comprising serial passaging viral strain SA2 in primary cell culture, preferably for between 5 and 30 passages, followed by serial passaging for 5 passages in embryohated eggs.

In a fourth aspect the present invention consists of a method of preventing infection by ILT virus in birds, comprising administering to a bird an effective dose of a vaccine containing an attenuated ILT virus, the attenuated virus being produced by serial passaging ILT SA2 virus, said virus characterised in that it produces an average pock diameter on chorio-allantoic membrane of commercial eggs of between 1.0 and 3 mm, the vaccine exhibits substantially reduced virulence in comparison to SA2 and causes substantially less weight loss in inoculated poultry in comparison to poultry similarly inoculated with SA2.

In an especially preferred embodiment of the present aspect of the invention the vaccine contains the deposited A20 strain or its functional equivalents.

BRIEF DESCRIPTION OF THE DRAWING

FIG. 1 illustrates the DNA profiles of three strains of ILT virus, including SA2 clone A at passage level 5 and 20, resulting from restriction endonuclease cleavage.

BEST MODE OF CARRYING OUT THE INVENTION

The invention will now be further described with reference to the following examples; Example 1
Production of Attenuated ILT SA2 viral vaccine was serially passaged 5 or 20 times on chicken kidney mono-layer cell cultures. These isolates were called Clone A passage 5 and Clone A passage 20 or A5 and A20 respectively. After 5 or 20 passages, the isolate was then serially passaged by inoculation into embryonated eggs via the dropped membrane route.

After 5 passages in embryonated eggs, the isolate was mixed with a suitable stabilizer for use as a vaccine.

Example 2

Characteristics of ILT Virus Clone A
1. Pock size on chorio-allantoic membranes of commercial eggs.

TABLE 1

| Virus | Average Pock Diameter (mm) | Standard Deviation |
|---|---|---|
| A5 | 2.18 | 0.54 |
| A20 | 2.28 | 0.68 |
| SA2 | 5.05 | 2.16 |
| Salisbury (Virulent) | 5.00 | 1.21 |

A5 and A20 pocks are uniformly small whilst SA2 pocks showed evidence of 2 populations—one small (Similar to Clone A) and one large (5–7 mm).

Clone A virus (A5 and A20) pocks are significantly ($P<0.001$) smaller than average size SA2 pocks and virulent virus pocks.

Virulent pocks are predominantly large, however some smaller (3 mm) pocks exist.

2. Virulence after intra-tracheal inoculation of 7 day old broiler chickens, monitored for 21 days after inoculation.

TABLE 2

| Expt. | Virus* | No. Birds Alive | No. Birds Dead | % Mortality+ |
|---|---|---|---|---|
| 1 | A5 | 25 | 0 | 0 |
|  | A20 | 20 | 0 | 0 |
|  | SA2 | 10 | 20 | 66.7 |
| 2 | A5 | 66 | 7 | 9.6 |
|  | A20 | 66 | 6 | 8.3 |
|  | SA2 | 48 | 64 | 57.1 |
| 3 | A5 | 78 | 2 | 2.5 |
|  | A20 | 77 | 3 | 3.8 |
|  | SA2 | 49 | 71 | 59.2 |
| 4 | A20 | 149 | 19 | 11.3 |
|  | SA2 | 103 | 65 | 38.7 |
| 5 | A20 | 116 | 5 | 4.1 |
|  | SA2 | 83 | 38 | 31.4 |

*all adjusted to 10,000 pfu/bird pfu = pock forming units
+all mortalities occurred within 7 days of inoculation 3. Virulence after eyedrop inoculation of day old commercial chickens vaccinated with 30,000 pfu/bird via eye drop.

TABLE 3

| Virus | Av. # Body Wt. 2 wk post vacc. (g) | No. Deaths Post Vacc. (ILT + ve)/Total |
|---|---|---|
| A5 | 221.4 | 1/39 |
| A20 | 224.9 | 0/41 |
| SA2 | 205.2 | 3/35 |
| Controls (unvaccinated) | 242.8 | 0/42 |
| #35–40 birds/group | | |

The SA2 vaccinated group was highly significantly lighter than controls ($p<0.001$).

Both A5 and A20 vaccinated groups were significantly lighter than controls ($p<0.05$).

The A20 vaccinated group had no deaths whereas SA2 post eyedrop showed 8.6% mortality (N. B. Some of the birds died of Mycoplasma infection during this experiment. Concurrent Mycoplasma infection may exacerbate the ILT virulence effect).

4. Protection Against Virulent ILT

TABLE 4

| Expt. | Virus | Vaccination Route | Vacc Dose+ | Challenge Route | % ILT Clinical Signs | % Deaths |
|---|---|---|---|---|---|---|
| A | A5 | Intra-tracheal | 10,000 | IT* | 4 | 0 |
|  | A20 | Intra-trachael | " | " | 10 | 0 |

TABLE 4-continued

| Expt. | Virus | Vaccination Route | Vacc Dose+ | Challenge Route | % ILT Clinical Signs | % Deaths |
|---|---|---|---|---|---|---|
|  | SA2 | Intra-trachael | " | " | 20 | 0 |
|  | Control | — | " | " | 100 | 70 |
| B | A5 | Ocular | 30,000 | IT* | 6.7 | 6.7 |
|  | A20 | " | " | " | 0 | 0 |
|  | SA2 | " | " | " | 4 | 0 |
|  | Control | — | — | " | 85 | 35 |
| C | A20 | Cloacal | 3,000 | C/i | 0 | — |
|  | A20 | " | 300 | " | 0 | — |
|  | A20 | " | 30 | " | 10 | — |
|  | A20 | " | 3 | " | 100 | — |
|  | Control | — | — | " | 88.9 | — |
| D | A20 | Cloacal | 30 | C/i | 20.4 | — |
|  | A20 | Ocular | " | " | 66.7 | — |
|  | A20 | Spray | " | " | 20 | — |
|  | A20 | Oral | " | " | 6.7 | — |
|  | Control | — | — | " | 73.3 | — |
| E | A20 | Ocular | 3,000 | IT* | 0. | 0 |
|  | SA2 | " | 10,000 | " | 0. | 0 |
|  | A20 | Spray | 3,000 | " | 33.3 | 16.7 |
|  | SA2 | " | 10,000 | " | 0 | 0 |
|  | A20 | Oral | 3,000 | " | 0 | 0 |
|  | SA2 | " | 10,000 | " | 0 | 0 |
|  | Control | — | — | " | 100 | 81.25 |

+pock forming units per bird
*IT = intratracheal, C/i - conjunctival instillation - no deaths expected via C/i.

Challenge was always with Salisbury strain virulent ILT at $10^3$ pfu/bird, except for the last experiment (E) when the challenge dose was $10^4$ pfu/bird.

In direct comparison with SA2 vaccine (expt. A,B & E) A20 vaccine was as good as or better than SA2 in protection against virulent ILT.

In all experiments A-D challenge occurred 2 weeks post vaccination. In experiment E challenge occurred 6 weeks post vaccination indicating a duration of immunity of at least 6 weeks.

Example 3

Restriction endonuclease differentiation of three strains of infectious laryngotracheitis virus (ILTV).

ILT virus strains may be differentiated by the use of DNA restriction endonuclease cleavage.

Fifteen different restriction eudonucleases were used in an attempt to differentiate between the SA2 clone A strain and its parent SA2, as well as the virulent Salisbury strain. The following table lists the restriction endonucleases and their cleavage sites.

TABLE 5

| Restriction Endonuclease | DNA Cleavage Sequence |
|---|---|
| BamHI | GGATCC |
| BglII | AGATCT |
| DraI | TTTAAA |
| EcoRI | GAATTC |
| EcoRV | GATATC |
| HincII | GTPyPuAC |
| HindIII | AAGCTT |
| HpAI | GTTAAC |
| KpnI | GGTACC |
| NaeI | GCCGGC |
| PstI | CTGCAG |
| SacI | GAGCTC |
| SmaI | CCCGGG |
| XbaI | TCTAGA |
| XhoI | CTCGAG |

(Restriction endonuclease cleavage carried out by Dr Michael Sheppard of the Commonwealth Scientific & Industrial Research Organistion, Division of Animal Health, Parkville, Melbourne).

All fifteen different restriction endonucleases differentiated between the virulent Salisbury strain and the SA2 and SA2 clone A strains. Four restriction endonucleases differentiated between all three strains (i.e., SA2, SA2 clone A, and Salisbury), but no restriction endonucleases differentiated between the passage 5 and 20 isolates of the SA2 clone A strain.

FIG. 1 illustrates the profiles achieved from DNA restriction endonuclease cleavage of the following three strains of ILT virus using BamHI, BglII, EcoRI and NaeI:

(i) SA2 strain (passage No. 2)
(ii) Salisbury strain; a virulent strain of ILT virus
(iii) SA2 clone A; passage 5 and passage 20 were compared From the results obtained, it is clear that the virulent Salisbury strain is very different from both SA2 and SA2 clone A. However, it is also clear that during the process of attenuation of SA2 to produce SA2 clone A, there have been significant changes in the genetic material of the virus so as to enable the differentiation of SA2 clone A from SA2 on the basis of restriction profiles.

Between SA2 and SA2 clone A, the BamHI restriction pattern showed a slight change in molecular weight of the first 3 bands and a unique 5th band for SA2. The BglII enzyme showed a unique second band for SA2 while EcoRI showed slight changes in the molecular weight of the second and third bands of SA2 compared with the two isolates of SA2 clone A. The enzyme NaeI showed SA2 to have a unique band between molecular weights 3.7 and 4.2 Kb.

Example 4

Field Trials

Field trials were undertaken to establish the safety and efficacy of a vaccine containing the ILT Clone A 20 as follows:

Field Trial No. 1—Safety and Efficacy in Layer Strain Birds

Approximately 11,450 7 day old birds were vaccinated with ILT A20 in the drinking water. The vaccine was reconstituted in 40 litres of drinking water containing 2.5 grams/L skim milk powder. The reconstituted vaccine was distributed via drinkers to the birds after 2 hours of water deprivation. The calculated dose per bird was 7,000 pfu/bird. Drinking water vaccine stability was monitored and found to be essentially unchanged 1 hour after reconstitution.

For a period of 8 days following vaccination the cause of all mortality was determined by veterinary staff by post mortem. All chickens were observed for clinical signs including conjunctivitis that may have been attributable to the vaccine. Normal commercial farm monitoring, including mortality, feed consumption and body weight was carried out.

Table 6 shows the mortality and cull figures for the 7 days before and 8 days after vaccination for the whole flock of birds. Post mortem examination showed that there was no mortality after vaccination as a result of ILT infection.

TABLE 6

BIRD MORTALITY BEFORE AND AFTER VACCINATION VIA DRINKING WATER WITH ILT A20

| Age (days) | Mortalities | Culls | Cumulative % of Total Flock | Comment |
|---|---|---|---|---|
| 1 | 11 | 2 | 0.11 | |
| 2 | 13 | | 0.22 | |
| 3 | 10 | | 0.31 | |
| 4 | 5 | 3 | 0.38 | |
| 5 | 14 | 2 | 0.52 | |
| 6 | 6 | 4 | 0.60 | |
| 7 | 5 | | 0.65 | Vaccination day ILT A20 |
| 8 | 5 | 2 | 0.71 | |
| 9 | 1 | | 0.72 | |
| 10 | 2 | | 0.73 | |
| 11 | 4 | | 0.77 | |
| 12 | 65 | | 1.33 | 0.55% smother |
| 13 | 1 | | 1.34 | |
| 14 | 15 | | 1.47 | Beak Trim |
| 15 | 14 | | 1.60 | |

Beginning at day 7 post vaccination beak trimming was carried out with no observable problems in the birds receiving the ILT A20 vaccine.

30 of the vaccinated chickens as well as 25 control unvaccinated chickens (from the same flock) were challenged at 4 weeks post vaccination (age of birds=5 weeks 1 day) with 10,000 pfu/bird of NSW virulent ILT administered by the eye drop route. A second group of 30 vaccinated birds and 25 unvaccinated birds were challenged at 46 days after vaccination when they were 7 weeks 4 days old using the same challenge method. The results of the chickens challenged post vaccination are given in Table 7.

TABLE 7

RESPONSE TO CHALLENGE OF BIRDS VACCINATED AT 7 DAYS OF AGE WITH ILT A20

| Group | Age at Weeks | Challenge Days | No of Birds Protected | Total No. of Birds | % Protected |
|---|---|---|---|---|---|
| Vaccinates | 5 | 1 | 24 | 30 | 80 |
| Controls | 5 | 1 | 0 | 25 | 0 |
| Vaccinates | 7 | 4 | 30 | 30 | 100 |
| Controls | 7 | 4 | 0 | 30 | 0 |

*Protection against challenge was assessed by absence of conjunctivitis in the challenged eye The results of this field trial show that:
1. The vaccine is easily administered to a large group of chickens via the drinking water.
2. No adverse effects were detectable post vaccination.
3. The vaccine proved highly efficacious. 80% of birds tested were protected at challenge at 5 weeks and 100% of birds tested were protected at challenge at 7 weeks, presumably the "true" proportion of the flock protected lies between 80% and 100%.

Field Trial 2

300,000 chickens in 25 flocks on 7 different commercial properties were vaccinated with ILT A20 in the drinking water using the same standard method as described in Field Trial 1 above. The age of the birds at vaccination ranged from 7 to 12 days.

In some flocks, as is standard practice, fowl pox vaccine was administered either pre or post ILT A20 administration. Also, beak trimming was carried out at various times as required within the various flocks, including the week following ILT A20 administration.

There were no post-vaccinaztion reactions detected and no problems attributable to the vaccine. The ILT A20 vaccine was found to be safe when used under these field conditions. Normal husbandry practices (beak trimming fowl pox vaccination etc.) did not induce ILT reactions in birds vaccinated with ILT A20.

Field Trial No.3—Safety and Efficacy in Broiler Strain Birds

In this commercial field trial 19,000 birds were vaccinated at 7 days of age with ILT A20 vaccine in the drinking water. The actual method of vaccination is the same as described in Field Trial No. 1. The calculated dose per bird was 5000 pfu. A comparable number of birds were used as unvaccinated on size controls. A number of birds were removed from the flock before vaccination to act as off-site controls in challenge studies described later.

The birds were monitored for a 10 day period following vaccination and the cause of all mortality was determined-the results are given in Table 8.

TABLE 8

MORTALITY IN BROILERS FOLLOWING VACCINATION WITH ILT A20 AT 7 DAYS

| Days Post Vaccination | On Site Controls | Vaccinates |
|---|---|---|
| 3 | 0/9* | 0/12 |
| 4 | 0/3 | 0/12 |
| 5 | 0/8 | 0/21 |
| 6 | 0/6 | 0/10 |
| 7 | 0/14 | 3/10 |
| 8 | 0/9 | 1/8 |
| 9 | 0/7 | 0/9 |
| 10 | 0/7 | 0/6 |

*Number with ILT lesions/Number dead from all causes

During the 10 days following vaccination there was no evidence of clinical ILT signs, conjunctivitis or other eye problems attributed to the vaccine. Post mortem examination showed that out of 19,000 birds vaccinated only 4 died with lesions consistent with ILT. Vaccination had no detectable effect on the birds' growth rate as measured by body weight—refer Table 9 (note that the body weights given are averages of the weights of 100 birds).

TABLE 9

BODY WEIGHTS (IN GRAMS) OF BROILER BIRDS DURING ILT A20 VACCINATION TRIAL

| Age (days) | On-Site Controls | Vaccinates | Target Weight+ | Percentage Difference* |
|---|---|---|---|---|
| 6 | | 113 | 130 | 13.1 |
| 14 | 330 | | 376 | 12.2 |
| 20 | | 571 | 685 | 16.6 |
| 26 | | 983 | 1161 | 15.3 |
| 28 | 1040 | | 1229 | 15.4 |
| 34 | | 1540 | 1705 | 9.7 |

+Ideal weight given as a performance goal
*Percentage difference of actual weight and target Two weeks after the birds were vaccinated 60 on-site controls, a number of off-site control birds and 60 vaccinated birds were challenged with virulent ILT administered by the eye drop route. A second challenge of 60 on-site controls, off-site controls and 60 vaccinates was carried out at 6 weeks of age (i.e. 5 weeks after vaccination). The results of this challenge are given in Table 10

TABLE 10

RESPONSE TO CHALLENGE OF BIRDS TWO WEEKS & FIVE WEEKS AFTER VACCINATION

| Group | Age at Challenge (days) | No. of Birds Protected* | Total No. of Birds | % Protected |
|---|---|---|---|---|
| Off-site controls | | | | |
| (a) | 21 | 0 | 22 | 0 |
| (b) | 28 | 0 | 28 | 0 |
| On-Site Controls | 28 | 7 | 60 | 11.7 |
| Vaccinates | 21 | 60 | 60 | 100 |
| Off-site controls | | | | |
| (a) | 42 | 0 | 18 | 0 |
| (b) | 42 | 0 | 30 | 0 |
| On-Site Controls | 42 | 4 | 60 | 6.7 |
| Vaccinates | 42 | 60 | 60 | 100 |

*Protection against challenge was assessed by absence of conjunctivitis in the challenged eye Table 10 shows that ILT A20 provided 100% protection in vaccinated birds. This protection persisted for the life of the bird.

The on site controls showed some protection possibly as a result of horizontal virus spread on the farm from the vaccinated birds. Protection of the on-site controls was low at first challenge (11.7%) and fell at the second challenge to 6.7% (which would be consistent with minimal horizontal spread). Off-site controls showed no protection whatsoever. The vaccinated group of birds showed 100% protection.

In summary, Field Trial No. 3 showed that:
1. The ILT A20 vaccine can be administered by the drinking water to a large flock of broiler chickens without any difficulties.
2. The ILT A20 vaccine is safe when used under field conditions in broiler chickens. The administration of the vaccine has minimal deleterious effects. Body weights, general mortality and culling levels were not delectably altered by the administration of the ILT A20 vaccine.,
3. The ILT vaccine proved to be highly efficacious. 100% of vaccinated birds were protected at challenge at 3 and 6 weeks of age (the age of the birds before processing is 6 weeks).

We claim:

1. An attenuted ILT virus, wherein said ILT virus:
   (1) produces an average pock diameter on chorioallantoic membrane of commercial eggs of between 1.0 and 3 mm,
   (2) exhibits substantially reduced virulence in comparsion to ILT SA2 strain;
   (3) causes substantially less weight loss in poultry in comparison to poultry infected with SA2;
   (4) elicits an immune response; and
   (5) the virus is ECAC V89042602.

2. A vaccine comprising an effective amount, sufficient to elicit an immune response, of the attenuated virus claimed in claim 1.

3. The vaccine as claimed in claim 2, further comprising a component selected from the group consisting of an excipient, a diluent stabilizer and a carrier.

4. The vaccine as claimed in claim 2, further comprising pharmaceutically acceptable compounds, and vaccines, used for vaccinations of birds.

5. The vaccine as claimed in claim 2, wherein the vaccine is formulated to be suitable for adminstration by oral, aerosol, eye drop or cloacal adminstration.

6. A method for preventing infection by ILT virus in birds comprising administering to a bird a vaccine which includes an effective amount, sufficient to elicit an immune response, of an attenuated virus strain as claimed in claim 1.

* * * * *

UNITED STATES PATENT AND TRADEMARK OFFICE
CERTIFICATE OF CORRECTION

PATENT NO. : 5,436,005
DATED : July 25, 1995
INVENTOR(S) : Trevor J. BAGUST and David R. McGAVIN It is certified that error appears in the above-indentified patent and that said Letters Patent is hereby corrected as shown below:

ON THE TITLE PAGE:
At [54] on the front page, change "INFECTIOUNS" to --INFECTIOUS--.

Column 1, line 36, change "for" to --from--.
Column 1, line 45, change "arian" to --avian--.
Column 1, line 53, change "pathoben" to --pathogen--.
Column 1, line 63, change "Arian" to --Avian--.

Column 2, line 5, change "vital" to --vaccine--.
Column 2, line 51, change "bryohated" to --bryonated--.

Column 3, line 6, change "ellicit" to --elicit--.
Column 3, line 27, change "embryohated" to --embryonated--.
Column 3, line 55, change "vital" to --viral--.

Column 5, line 47, change "eudonucleases" to --endonuclease--.

Column 8, line 1, change "vaccinaztion" to --vaccination--.

UNITED STATES PATENT AND TRADEMARK OFFICE
CERTIFICATE OF CORRECTION

PATENT NO. : 5,436,005
DATED : July 25, 1995
INVENTOR(S) : Trevor J. BAGUST and David R. McGAVIN It is certified that error appears in the above-indentified patent and that said Letters Patent is hereby corrected as shown below:

Column 10, line 2, change "delectably" to --detectably--.
Column 10, lines 14 and 15, change "comparsion" to --comparison--.

Signed and Sealed this

Second Day of April, 1996

BRUCE LEHMAN

Attest:

Attesting Officer

Commissioner of Patents and Trademarks